US011045264B2

(12) United States Patent
Yen et al.

(10) Patent No.: US 11,045,264 B2
(45) Date of Patent: Jun. 29, 2021

(54) CONTROL METHOD FOR CONTROLLING A ROBOT FOR ORTHOPEDIC SURGERY

(71) Applicants: NATIONAL TAIWAN UNIVERSITY, Taipei (TW); TAIPEI TZU CHI HOSPITAL, BUDDHIST TZU CHI MEDICAL FOUNDATION, New Taipei (TW)

(72) Inventors: Ping-Lang Yen, Taipei (TW); Shuo-Suei Hung, New Taipei (TW)

(73) Assignees: NATIONAL TAIWAN UNIVERSITY, Taipei (TW); TAIPEI TZU CHI HOSPITAL, BUDDHIST TZU CHI MEDICAL FOUNDATION, New Taipei (TW)

( * ) Notice: Subject to any disclaimer, the term of this patent is extended or adjusted under 35 U.S.C. 154(b) by 602 days.

(21) Appl. No.: 15/397,742

(22) Filed: Jan. 4, 2017

(65) Prior Publication Data
US 2017/0112579 A1    Apr. 27, 2017

Related U.S. Application Data

(62) Division of application No. 14/228,726, filed on Mar. 28, 2014, now Pat. No. 9,561,082.

(30) Foreign Application Priority Data

Dec. 30, 2013    (TW) .................................. 102149096

(51) Int. Cl.
*A61B 34/30*    (2016.01)
*A61B 17/16*    (2006.01)
(Continued)

(52) U.S. Cl.
CPC .............. *A61B 34/30* (2016.02); *A61B 17/16* (2013.01); *A61B 17/1622* (2013.01);
(Continued)

(58) Field of Classification Search
CPC ..... A61B 34/30; A61B 17/16; A61B 17/1626; B25J 9/10; B25J 9/1005; B25J 9/16; B25J 9/1623; B25J 17/02; B25J 17/0216
See application file for complete search history.

(56) References Cited

U.S. PATENT DOCUMENTS 8,029,510 B2    10/2011    Hoegerle
2007/0260255 A1*  11/2007    Haddock ............ A61B 17/3421
                                                606/80
(Continued)

FOREIGN PATENT DOCUMENTS

CN    101443162 A    5/2009
DE    3800482 A1     7/1989
(Continued)

*Primary Examiner* — Christopher J Beccia
(74) *Attorney, Agent, or Firm* — Muncy, Geissler, Olds & Lowe, P.C.

(57) ABSTRACT

The present invention provides a handheld robot for orthopedic surgery and a control method thereof. The handheld robot of the present invention includes a main body, a grip, a kinematic mechanism, a tool connector, a tool, a force sensor and a positioning unit. The handheld robot of the present invention combines the position/orientation information of the tool acquired by the positioning unit with the force/torque information acquired by the force sensor, and utilizes the combined information to adjust the position of the tool so as to keep the tool within the range/path of a predetermined operation plan. In this way, the precision of the orthopedic surgery can be enhanced, and the error occurred during the surgery can be minimized.

15 Claims, 17 Drawing Sheets

(51) Int. Cl.
  *A61B 17/17*    (2006.01)
  *A61B 17/88*    (2006.01)
  *G05B 15/02*    (2006.01)
  *A61B 34/00*    (2016.01)
  *A61B 34/20*    (2016.01)
  *B25J 1/00*     (2006.01)
  *B25J 9/10*     (2006.01)
  *B25J 9/16*     (2006.01)
  *B25J 15/00*    (2006.01)
  *B25J 17/02*    (2006.01)
  *A61B 17/15*    (2006.01)
  *A61B 90/00*    (2016.01)

(52) U.S. Cl.
  CPC ...... *A61B 17/1626* (2013.01); *A61B 17/1703* (2013.01); *A61B 17/8875* (2013.01); *A61B 34/20* (2016.02); *A61B 34/75* (2016.02); *A61B 34/76* (2016.02); *B25J 1/00* (2013.01); *B25J 9/1005* (2013.01); *B25J 9/1623* (2013.01); *B25J 15/0019* (2013.01); *B25J 17/0216* (2013.01); *G05B 15/02* (2013.01); *A61B 17/155* (2013.01); *A61B 2034/2055* (2016.02); *A61B 2034/304* (2016.02); *A61B 2090/061* (2016.02); *A61B 2090/064* (2016.02); *A61B 2090/066* (2016.02); *A61B 2090/08021* (2016.02)

(56) References Cited

U.S. PATENT DOCUMENTS

| | | | |
|---|---|---|---|
| 2008/0077149 A1* | 3/2008 | Hoegerle | A61B 17/1613 606/80 |
| 2012/0143084 A1* | 6/2012 | Shoham | A61B 17/1675 600/567 |
| 2013/0096574 A1 | 4/2013 | Kang | |
| 2013/0116706 A1* | 5/2013 | Lee | A61B 34/30 606/130 |
| 2013/0317355 A1 | 11/2013 | Jacobsen et al. | |
| 2014/0039681 A1* | 2/2014 | Bowling | A61B 34/32 700/261 |

FOREIGN PATENT DOCUMENTS

| | | |
|---|---|---|
| DE | 102004038414 A1 | 3/2006 |
| EP | 1929964 A1 | 10/2009 |
| TW | 200724331 A | 7/2007 |
| TW | 200800123 A | 1/2008 |
| TW | 200821888 A | 5/2008 |
| TW | 201143708 A | 12/2011 |
| WO | 2011021192 A1 | 2/2011 |
| WO | 2011143016 A1 | 11/2011 |
| WO | 2013067535 A1 | 5/2013 |
| WO | 2013138481 A1 | 9/2013 |

* cited by examiner

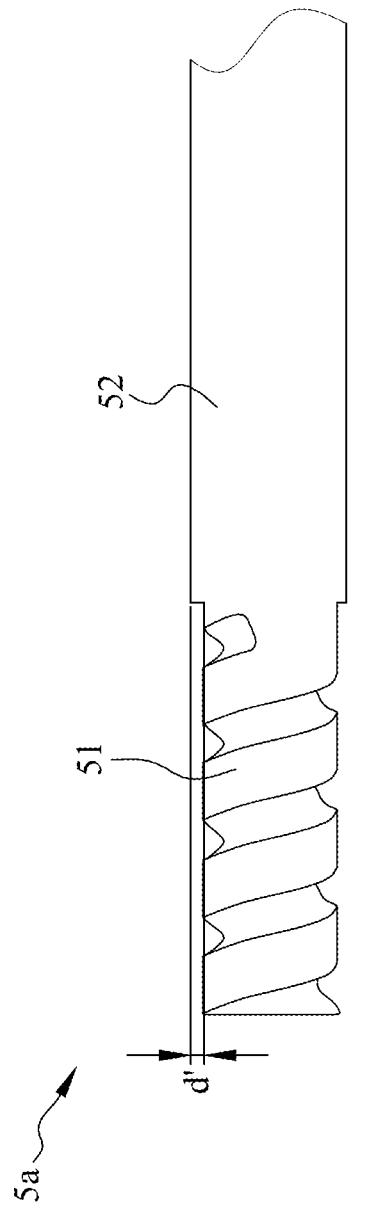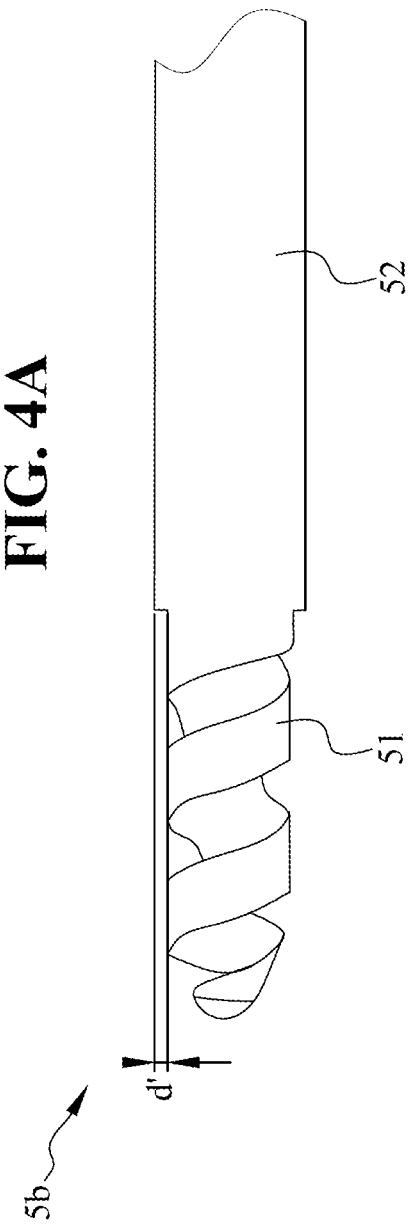

CONTROL METHOD FOR CONTROLLING A ROBOT FOR ORTHOPEDIC SURGERY

CROSS-REFERENCE TO RELATED APPLICATION

The present application is a Divisional Application of the U.S. application Ser. No. 14/228,726, filed Mar. 28, 2014, which claims priority to Taiwan Application Serial Number 102149096, filed Dec. 30, 2013, all of which are herein incorporated by reference.

BACKGROUND OF THE INVENTION

1. Field of the Invention

The present invention relates generally to a surgical robot, and more particularly, to a handheld robot for orthopedic surgery and the control method thereof. The handheld robot of the present invention is able to combine the position/orientation information of a tool acquired by a positioning unit with the force/torque information acquired by a force sensor, and is able to utilize the combined information to compensate the motion of the handheld robot.

2. The Prior Arts

In the field of orthopedic surgery, surgical jigs, computer aided navigation program or image-guided robotic arm are commonly used to assist surgeons to position the bones during the operation, such as an osteotomy, or surgeries that requires the surgeon to place plant bone plates or bone screws into patients.

In a surgery where surgical jigs are used to help with the measuring and the positioning of the cut, surgeons often need to switch surgical jigs during one operation multiple times, which can lead to errors in the positioning. In addition, the use of a surgical jig also depends on factors such as the familiarity of the surgeon with the surgical jig, the level of operation technique of the surgeon and clinical experience of the surgeon. In orthopedic surgeries where computer aided navigation program is used for positioning, the navigation program guides the surgeon to position/orientate the cutting block, so as to mount the cutting block on the bones of the patient. However, in the actual surgeries, surgeons need to constantly adjust the cutting block manually to position/orientate the cutting block as instructed by the navigation program, which complicates the positioning process. In recent years, some solutions have been developed addressing the abovementioned issue. For example, an adjusting screw can be used to finely adjust the position/orientation of the cutting block. However, in the process of mounting the cutting block with the adjusting screw, the precision of the result might still be compromised due to the error occurred during the process of fixing the adjusting screw.

In orthopedic surgeries with image-guided robotic arms, medical images and robotics are used for the positioning. Before the surgery is performed, surgeons would acquire computer tomography (CT) image first so as to prepare the surgery by planning the operation path. During the surgery, first, the bone of the patient is immobilized, and a position system is used to monitor if the bone is moving. If the bone of the patient moved during the operation, the positioning system immediately starts the re-coordination procedure to ensure the precision and the safety of the operation. Alternatively, surgeons can utilize the positioning system to measure the relative position and orientation between the bone and the robotic arm, and further perform precise positioning and bone cutting through dynamic motion compensation control. Herein, the optical positioning system is one of the most commonly used positioning systems in the medical industry. The optical positioning system utilize an optical tracker to tack the light-reflecting balls disposed on the bones and the robotic arm, thereby determining information such as the relative position, relative orientation and relative speed between the robotic arm and the patient. Subsequently, the image-guided robotic arm use the above information along with a control method to determine if the parameters of the patient and the equipment are compliant with the surgical procedure, and further compensate the position and orientation of the tool with regard to the patient. However, due to the response bandwidth of the optical positioning system, the reaction speed of the robotic arm is limited, which compromises the precision of the operation. In addition, blockage is a more serious matter which occurs quite often in the optical positioning system. When the light-reflecting balls are blocked by obstacles, the optical positioning system cannot provide the relative position and orientation between the bones and the robotic arm. Hence, in the situation where only optical positioning system is used to assist with the motion compensation of the robotic arm, the position of the robotic arm cannot be adjusted in time, which can endanger the safety of the patient. Furthermore, compared with the conventional bone cutting tool, the size of the robotic arm is way too huge, which causes inconveniences for the surgeons, and also limits the application thereof.

On the other hand, in the conventional control methods for robotic arms that utilizes medical images and positioning information to compensate the motion thereof, in order to prevent the tool from damaging the blood vessels, nerves or soft tissues of the patient, current control methods simply turn off the motor when the front end of the tool deviates from the predetermined operation range/path. Such control methods lack the ability to keep the front end of the tool within the range/path of the operation plan; therefore, surgeons need to control the movement of the robotic arm manually throughout the whole operation process, which can be very exhausting.

SUMMARY OF THE INVENTION

Based on the above reasons, a primary objective of the present invention is to provide a handheld robot for orthopedic surgeries. The handheld robot provided by the present invention is able to combine the relative position/orientation information between a tool and a bone acquired by a positioning unit with the force/torque information feedback by the bone acquired by a force sensor, and is able to utilize the combined information to compensate the motion of the handheld robot in a quick and timely manner, so as to keep the tool within the range/path of a predetermined operation plan. As a result, the precision of the orthopedic surgery can be enhanced, and the error occurred during the surgery can be minimized.

Another objective of the present invention is to provide a tool specifically designed for further detecting a deviation force between the bone and the tool. With the design of the present invention, the sensitivity of the motion compensation of the tool is improved, thereby preventing the tool from deviating from the path of the predetermined operation plan.

For achieving the foregoing objectives, the present invention provides a handheld robot for orthopedic surgery. The handheld robot includes: a main body, a grip, a kinematic mechanism, a tool connector, a tool, a force sensor and a positioning unit. The main body has an inner space. The grip is connected at a side of the main body. The kinematic mechanism has six degrees of freedom and is disposed inside the inner space of the main body. The kinematic mechanism at least includes a stationary plate, a mobile plate and a plurality of actuating units. The actuating units are mounted on the stationary plate and are connected with the mobile plate via a plurality of connecting rods. The tool connector is disposed on the mobile plate. The tool has a threaded segment and a non-threaded segment, and is connected at the tool connector. The threaded segment has a first diameter, the non-threaded segment has a second diameter, and the first diameter is smaller than the second diameter. The force sensor is disposed between the tool connector and the mobile plate. The positioning unit is disposed on the mobile plate for positioning the position and orientation of the tool. The force sensor measures a force, which is parallel to an axial direction of the tool, between an object and the tool, and the force sensor further measures a deviation force between the tool and the object in coordination with the difference in the diameters between the threaded segment and the non-threaded segment. The handheld robot as described combines a position/orientation information acquired by the positioning unit with the force/deviation force information measured by the force sensor, and adjusts the position and orientation of the tool based on a combined information.

According to an embodiment of the present invention, the kinematic mechanism further includes a motor mounting plate mounted on the stationary plate. In addition, each of the actuating unit includes: a motor, a coupling, a lead screw and a slider. The motor is disposed on the motor mounting plate. The coupling is disposed between the motor and the motor mounting plate. The lead screw is connected to the motor. The slider is engaged with the lead screw via a sliding block, wherein an end of the slider is connected with the connecting rod via a joint. When the motor drives the lead screw to rotate, the lead screw also drives the slider to slide in a linear direction through the sliding block.

According to an embodiment of the present invention, the positioning unit is a plurality of light-reflecting balls; wherein the light-reflecting balls positions the position and orientation of the tool in coordination with an optical positioning system. Herein, the positioning unit can also be other conventional positioning unit, such as an electromagnetic positioning system or an inertia measurement unit (IMU).

According to an embodiment of the present invention, the tool connector includes a spindle motor for driving the tool to rotate.

According to an embodiment of the present invention, another force sensor is disposed between the grip and the main body for measuring the force applied by the user when operating the handheld robot.

In addition, the present invention provides a control method for controlling the handheld robot for orthopedic surgery as described above. The control method of the present invention includes the following steps: preparing an operation plan with a predetermined range/path; acquiring a position/orientation information of a tool, which is disposed at a front end of the handheld robot, with a positioning unit, and adjusting the position/orientation of the tool based on the position/orientation information acquired, so as to keep the tool within the predetermined range/path of the operation plan; and measuring a force/torque between the tool and an object with a force sensor, and adjusting the position/orientation of the tool based on the measured force/torque, so as to keep the tool within the predetermined range/path of the operation plan. The force/torque measured by the force sensor includes a deviation force between the tool and the object.

According to an embodiment of the present invention, the control method further include a step of combining the position/orientation information acquired by the positioning unit with the force/torque information measured by the force sensor, and adjusting the position/orientation of the tool based on a combined information.

According to an embodiment of the present invention, the tool includes a threaded segment and a non-threaded segment. The threaded segment has a first diameter, the non-threaded segment has a second diameter, and the first diameter is smaller than the second diameter.

According to an embodiment of the present invention, when the robot is used for drilling, the deviation force/torque includes a force/torque orthogonal to an axial direction of the tool. In addition, the method further comprises calculating a drilling force/torque, which is a force/torque parallel to the axial direction of the tool, to determine if the drilling is completed.

According to an embodiment of the present invention, when the robot is used for cutting, the deviation force/torque includes a force parallel to a normal vector of a cutting surface, and also includes two torques that are orthogonal to the normal vector of the cutting surface. In addition, the method further comprises calculating a cutting force/torque, which are a force parallel to the cutting surface and a torque orthogonal to the cutting surface, to determine if the cutting is completed.

BRIEF DESCRIPTION OF THE DRAWINGS

The present invention will be apparent to those skilled in the art by reading the following detailed description of a preferred embodiment thereof, with reference to the attached drawings, in which:

FIG. 4A and FIG. 4B are enlarged views of a tool according to the preferred embodiment of the present invention, respectively;

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
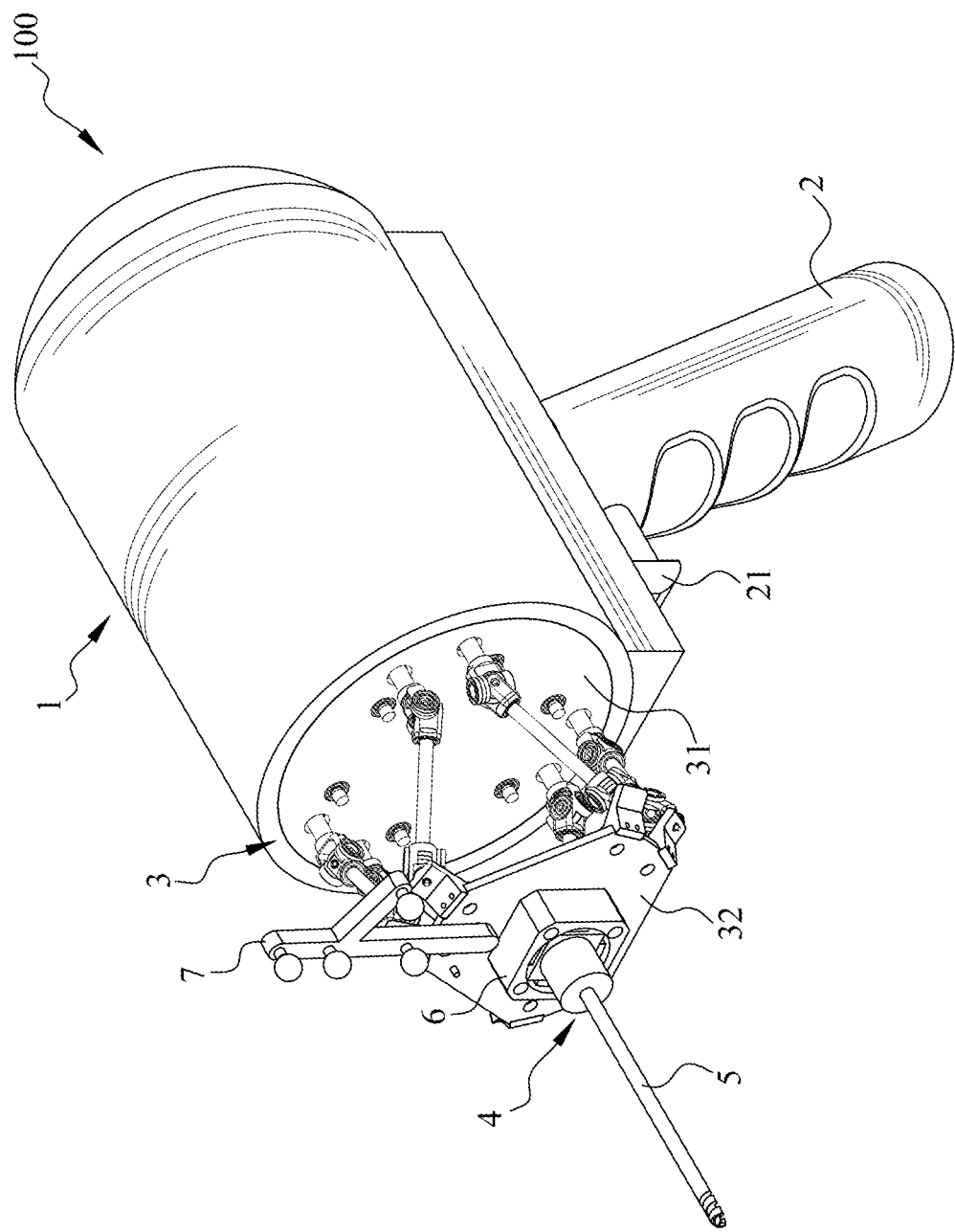
FIG. 1 is a perspective view of a handheld robot for orthopedic surgery according to a preferred embodiment of the present invention.

FIG. 1 is a perspective view showing a handheld robot 100 for orthopedic surgery of the present invention. As shown in FIG. 1, the handheld robot 100 according to a preferred embodiment of the present invention 100 includes: a main body 1, a grip 2, a kinematic mechanism 3, a tool connector 4, a tool 5, a force sensor 6 and a positioning unit 7.

Figure 2:
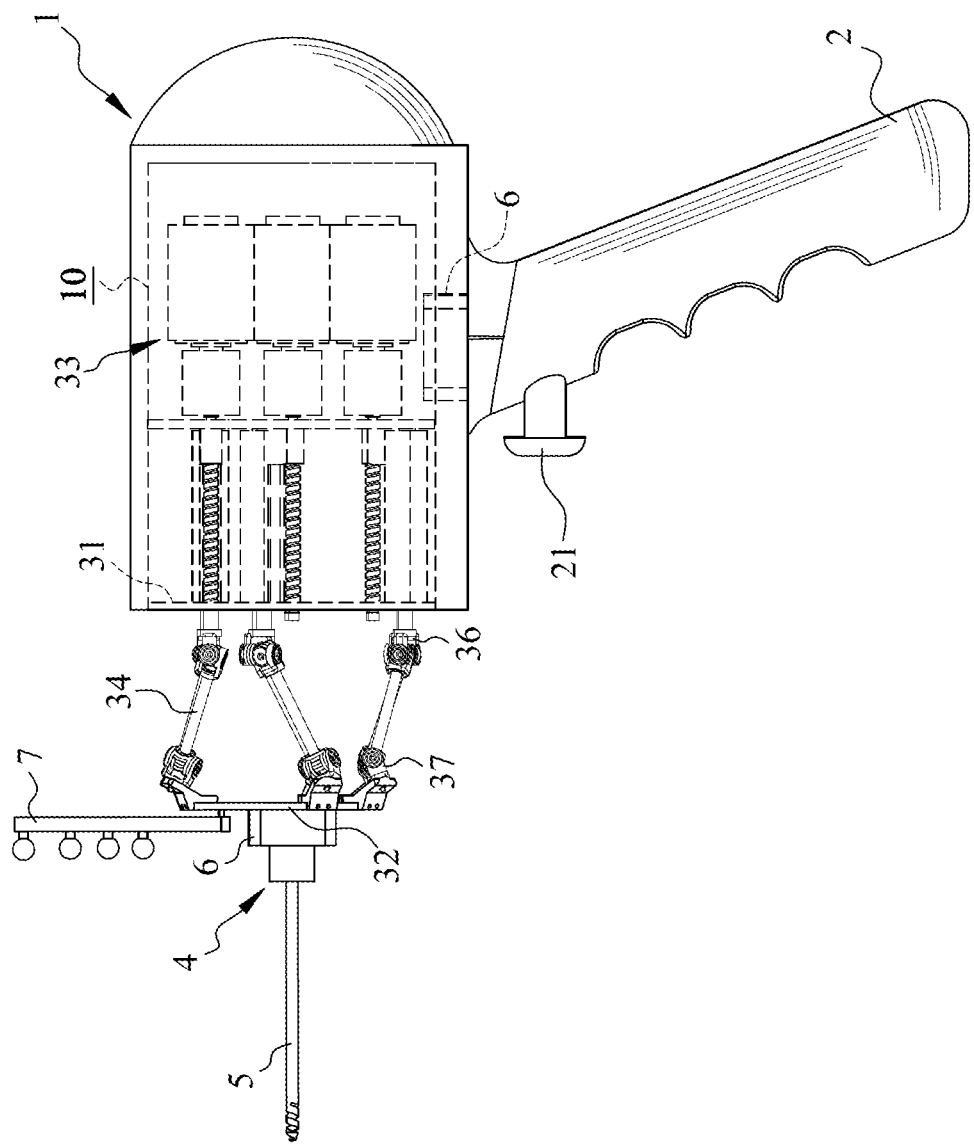
FIG. 2 is a side view of the handheld robot according to the preferred embodiment of the present invention.
Figure 3:
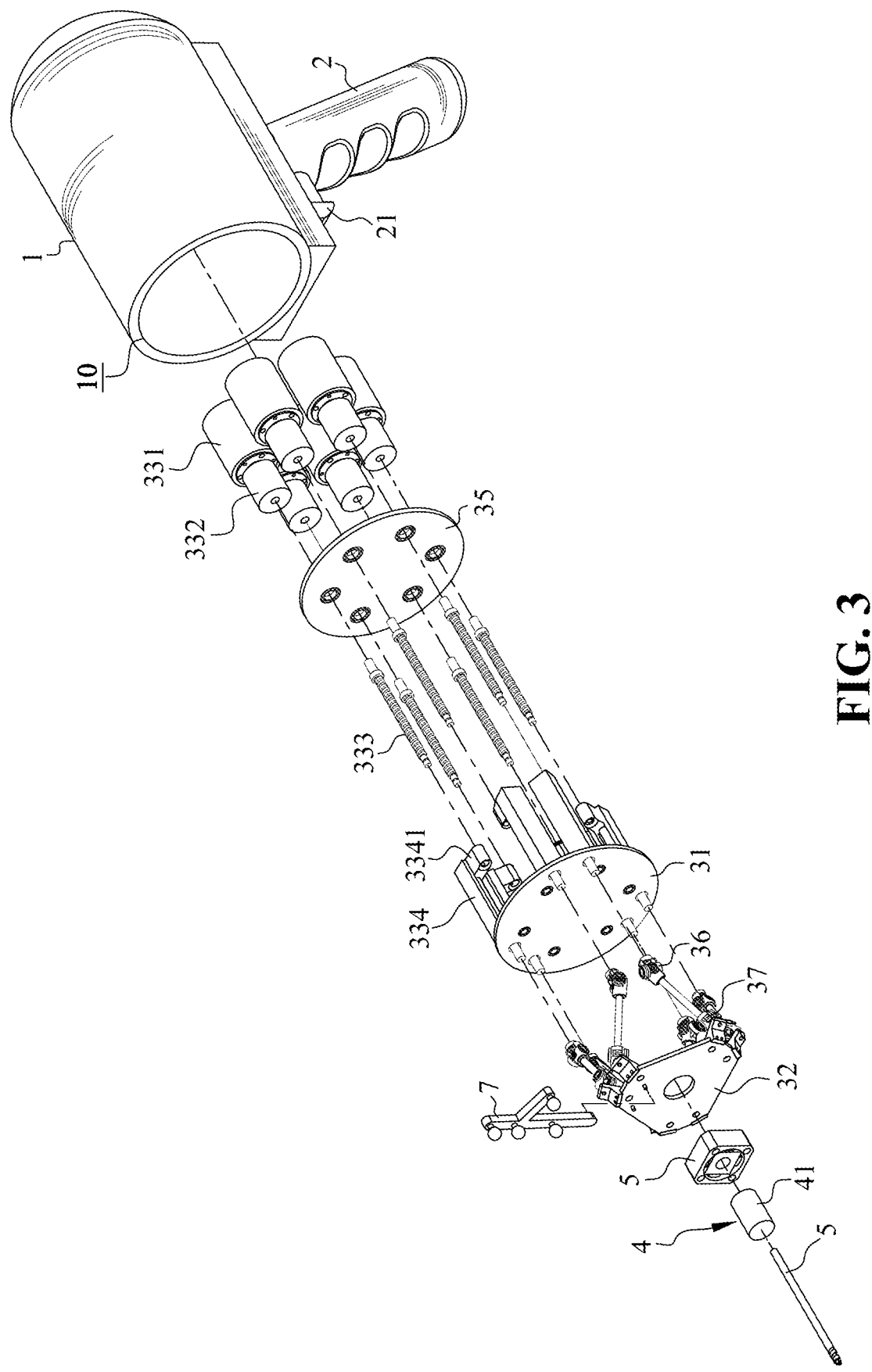
FIG. 3 is an exploded and perspective view of the handheld robot according to the preferred embodiment of the present invention.

FIG. 2 is a side view showing the handheld robot 100 according to the preferred embodiment of the present invention, and FIG. 3 is an exploded and perspective view of the handheld robot 100 according to the preferred embodiment of the present invention. As shown in FIG. 1~FIG. 3, the main body 1 has an inner space 10, and the grip 2 is connected at a side of the main body 1 for a user to grip on. A button 21 is disposed on the grip 2 for turning on or turning off the handheld robot 100. The kinematic mechanism 3 has six degrees of freedom, and is disposed inside the inner space 10 of the main body 1. The kinematic mechanism 3 at least includes a stationary plate 31, a mobile plate 32 and a plurality of actuating units 33. The actuating units 33 are mounted on the stationary plate 31, and are connected with the mobile plate 32 via a plurality of connecting rods 34. The structure and actuation method of the kinematic mechanism 3 will be described in details in the following sections.

In the preferred embodiment of the present invention, the kinematic mechanism 3 is a parallel mechanism with six degrees of freedom. Due to the features of the parallel mechanism, such as high stability in structure, high rigidity, zero accumulative error, small inertia and small working space, the parallel mechanism is best suited for surgical equipment, which requires high accuracy and small working space.

As shown in FIG. 2 and FIG. 3, the kinematic mechanism 3 according to the preferred embodiment of the present invention further includes a motor mounting plate 35. The motor mounting plate 35 is mounted on the stationary plate 31 with a distance therebetween. Each of the actuating unit 33 includes: a motor 331, a coupling 332, a lead screw 333 and a slider 334. The motor 331 is disposed on the motor mounting plate 35. The coupling 332 is disposed between the motor 331 and the motor mounting plate 35. The lead screw 33 is connected to the motor 331 through the motor mounting plate 35 and the coupling 332. The slider 334 is engaged with the lead screw 333 via a sliding block 3341, wherein an end of the slider 334 is connected with the connecting rod 34 via a joint 36. Herein, the joint 36 has two degrees of freedom. The other end of the connecting rod 34 is connected with the mobile plate 32 through a joint 37, which has three degrees of freedom. When the motor 331 drives the lead screw 333 to rotate, the lead screw 333 also drives the slider 334 to slide in a linear direction through the sliding block 3341, and further actuates the connecting rod 34. In the preferred embodiment of the present invention, there are six actuating units 33 in the kinematic mechanism 3. With the above configuration, when the actuating units 33 actuate the connecting rods 34, the mobile plate 32 is driven to move or rotate to different positions/orientations, thereby moving the tool 5 to a desired position/orientation.

As shown in FIG. 2 and FIG. 3, the tool connector 4 is disposed on the mobile plate 32, and the tool 5 is connected at the tool connector 4. In the handheld robot 100 of the present invention, tool 5 can be replaced with suitable tools according to the purpose of each operation. For example, in an osteotomy, a milling cutter can be used as the tool 5; when tightening bone screws, a screw driver tool can be used as the tool 5; and when the handheld robot 100 is used for drilling, a drill bit can be used as the tool 5. The tool connector 4 includes a spindle motor 41 for driving the tool 5 to rotate. The force sensor 6 is disposed between the tool connector 4 and the mobile plate 32 for measuring the force/torque generated between the tool and the bone during the operation.

Herein, it is worth mentioning that the tool 5 according to the preferred embodiment of the present invention has been designed specifically to enhance the sensitivity of the force sensor 6. FIG. 4A is an enlarged view showing a front end of a milling tool 5a according to the preferred embodiment of the present invention, and FIG. 4B is an enlarged view showing a front end of a drilling tool 5b according to the preferred embodiment of the present invention. As shown in FIG. 4A and FIG. 4B, the milling tool 5a and the drilling tool 5b both include a threaded segment 51 and a non-threaded segment 52. The threaded segment 51 of the tools has a first diameter, and the non-threaded segment 52 of the tools has a second diameter. As can be seen in the figures, the first diameter is smaller than the second diameter, and a diameter difference d' exists between the threaded segment 51 and the non-threaded segment 52.

Under the situation where normal tools are used, the force sensor 6 is only able to measure the force that is directly exerted on the tool by the bones of the patient; in other words, the force sensor 6 is only able to measure the force which is parallel to an axial direction of the tool. However, if the tool offsets or deviates from the path of a predetermined operation plan when the threaded segment drills into the bones, it is more difficult for force sensor to detect the deviation force exerted on the tool by the bone with conventional tools, that is, it is more difficult to detect the force/torque orthogonal to the axial direction of the tool. As a result, it is more difficult for the force sensor 6 to detect the situation in which the tool offsets from the path of a predetermined operation plan, or the situation in which the tool deviates from the path of a predetermined operation plan with an angle. With the specially designed tool 5 of the present invention, the bone of the patient will collide with the diameter difference d' between the threaded segment 51 and the non-threaded segment 52 when the threaded segment 51 of the tool 5 drills through the bones, and a deviation force is generated therebetween. In other words, the force sensor 6 would detect a force that is orthogonal to the axial direction of the tool 5, or the force sensor 6 would detect a torque generated between the bones and the tool 5. In this way, the sensitivity of the force sensor 6 can be enhanced.

As shown in FIG. 2 and FIG. 3, the positioning unit 7 is disposed on the mobile plate 32 for positioning the position and orientation of the tool 5. The positioning unit 7 can be any conventional positioning systems, such as an optical positioning system, an electro-magnetic positioning system or an inertia measurement unit. In the preferred embodiment of the present invention, the positioning unit is a plurality of light-reflecting balls, which can track the position and orientation of the tool 5 when used with an optical positioning system. In addition, another force sensor 6 can be disposed between the grip 2 and the main body 1 to further measure the force exerted by the hand of the user during the operation.

Figure 5:
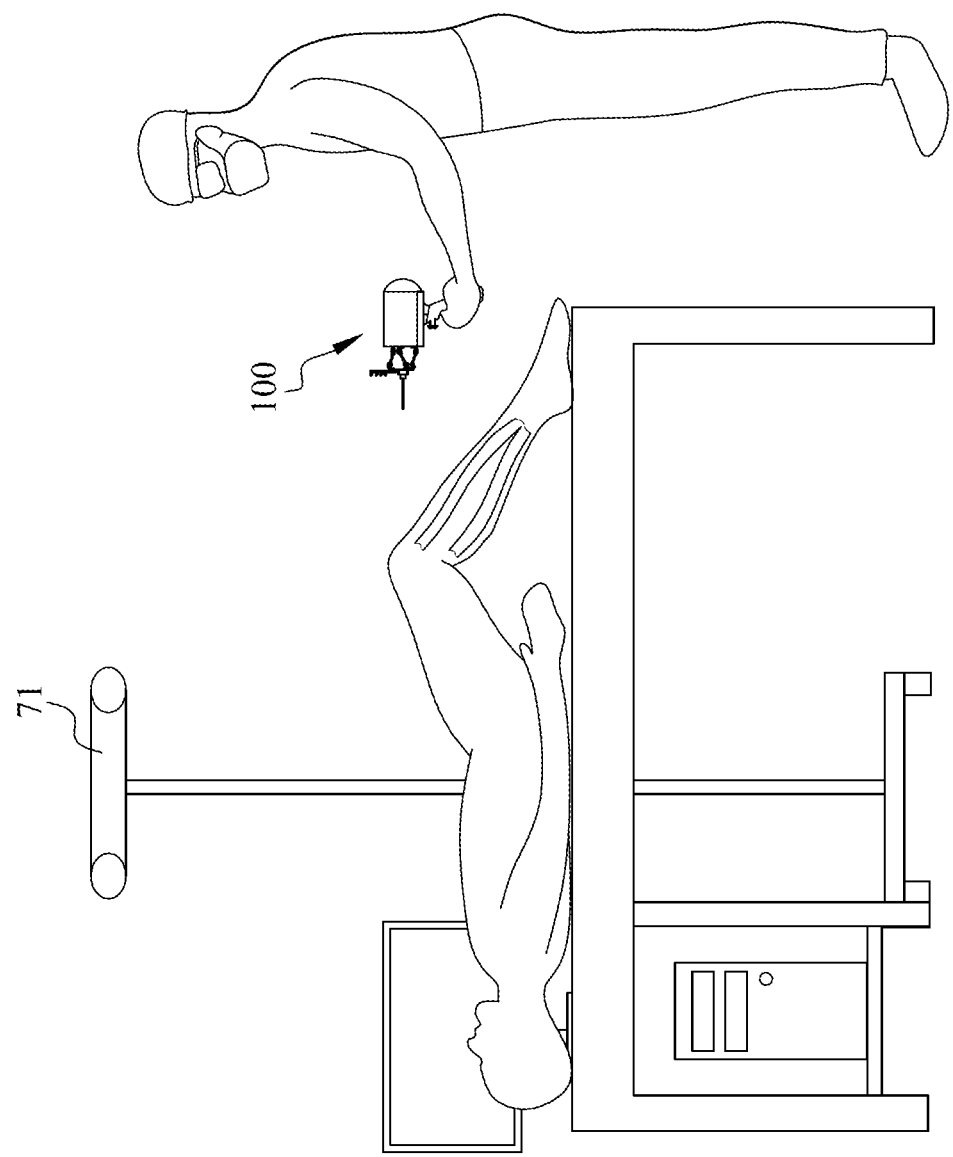
FIG. 5 is schematic view illustrating the handheld robot of the present invention being used in a surgery according to the preferred embodiment.

FIG. 5 is schematic view illustrating the handheld robot 100 of the present invention being used in a surgery according to the preferred embodiment. As shown in FIG. 5, when the handheld robot 100 of the present invention is in use, a user holds the handheld robot 100 with his/her hand and operate on the bones of a patient according to a predetermined operation plan. Because the kinematic mechanism 3 of the handheld robot 100 is a parallel mechanism, the size of the handheld robot 100 is smaller compared to conventional mechanical robotic arms, and the agility of the handheld robot 100 is also higher when in use. During an operation, the handheld robot 100 is used in coordination with an optical positioning system 71 to track the positioning unit 7 disposed on the mobile plate 32, so as to determine the relative position and orientation of the tool 5 with regard to the bones. In addition, when the tool 5 comes into contact with the bone of the patient, the force sensor 6 measures the force and torque between the tool and the bone to further determine the relative position and orientation of the tool 5 with regard to the bone. In this way, the handheld robot 100 combines the position/orientation information of the tool 5 acquired by the positioning unit 7 with the force/torque information measured by the force sensor 6, and utilizes the combined information to adjust the position of the tool 5 so as to keep the tool 5 within the range/path of a predetermined operation plan.

With reference to the figures, cases in which the handheld robot 100 of the present invention is used in different operations will be explained in details in the following section.

Figure 6:
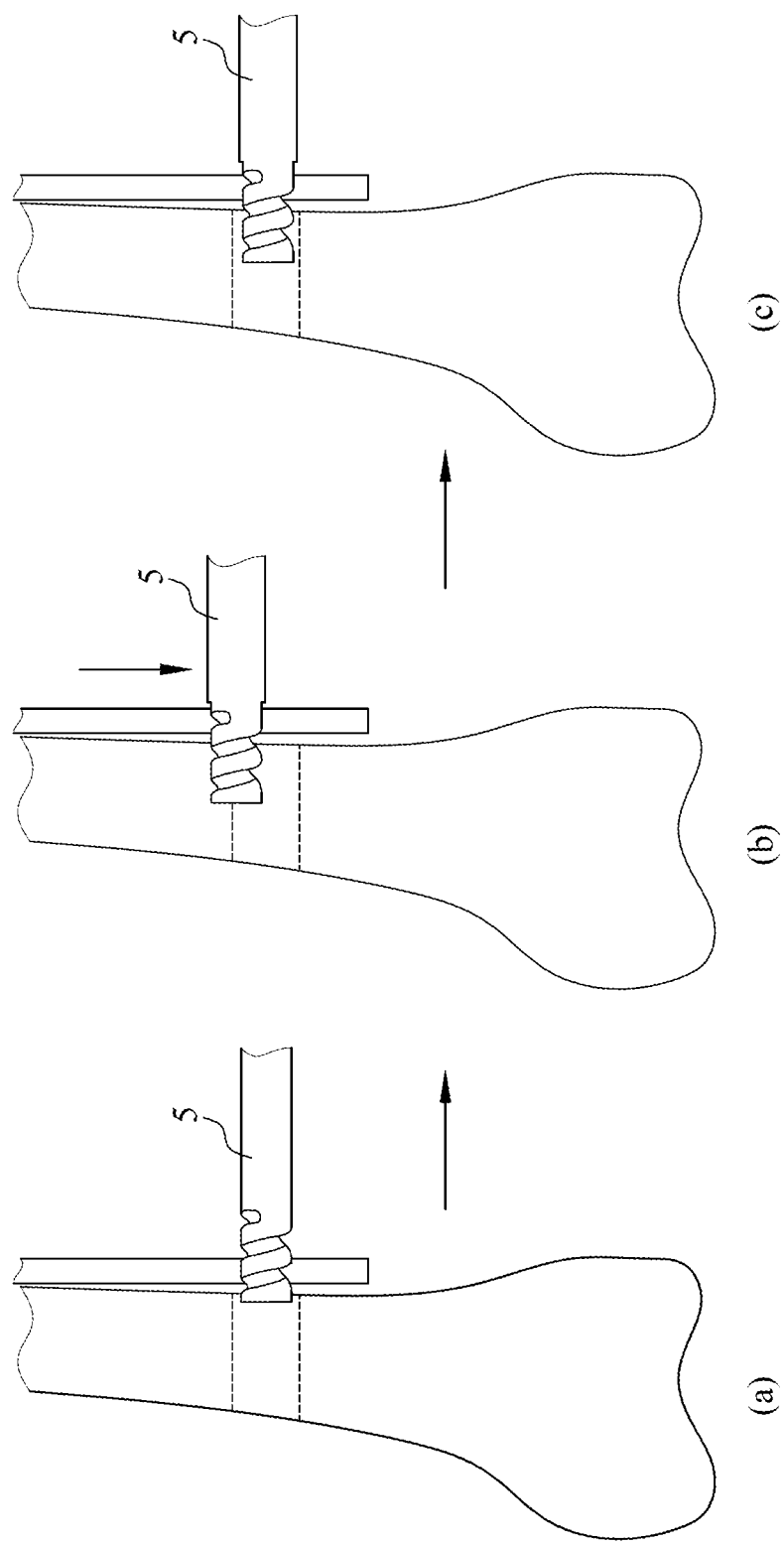
FIG. 6 is a schematic view illustrating the handheld robot of the present invention being used for drilling in a bone plate fixation surgery, wherein the tool offsets from the path of a predetermined operation plan.
Figure 7:
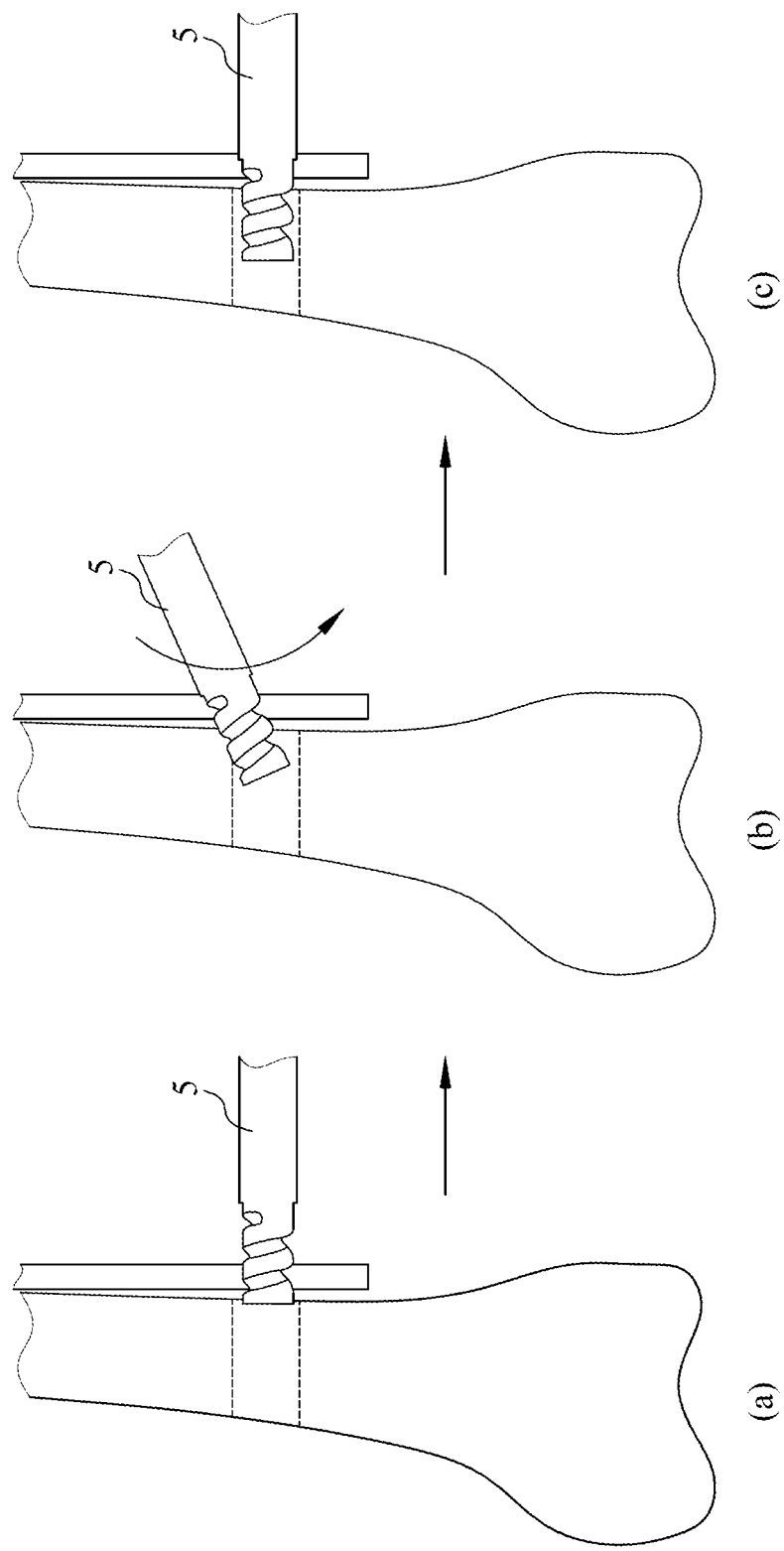
FIG. 7 is a schematic view illustrating the handheld robot of the present invention being used for drilling in the bone plate fixation surgery, wherein the tool deviates from the path of the predetermined operation plan with an angle.
Figure 8:
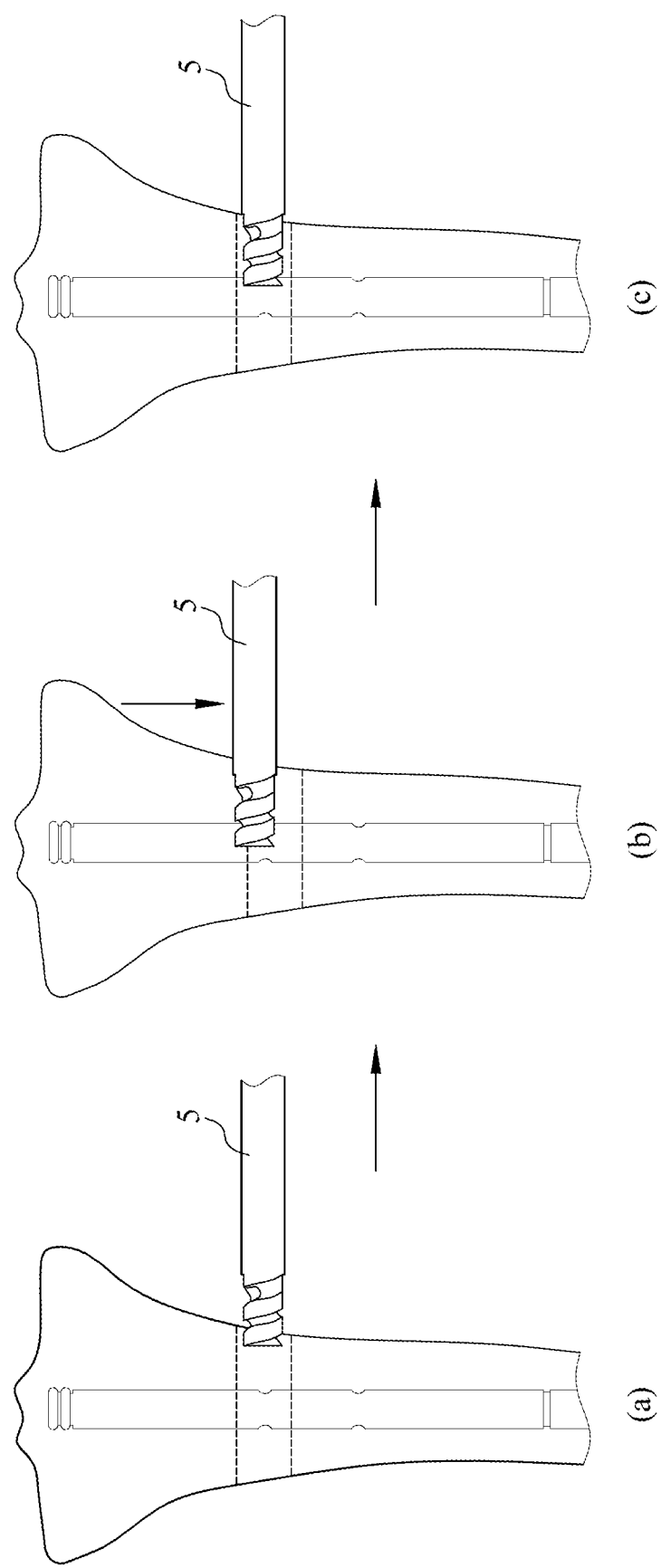
FIG. 8 is a schematic view illustrating the handheld robot of the present invention being used for drilling in an intramedullary interlocking screw fixation surgery, wherein the tool offsets from the path of a predetermined operation plan.
Figure 9:
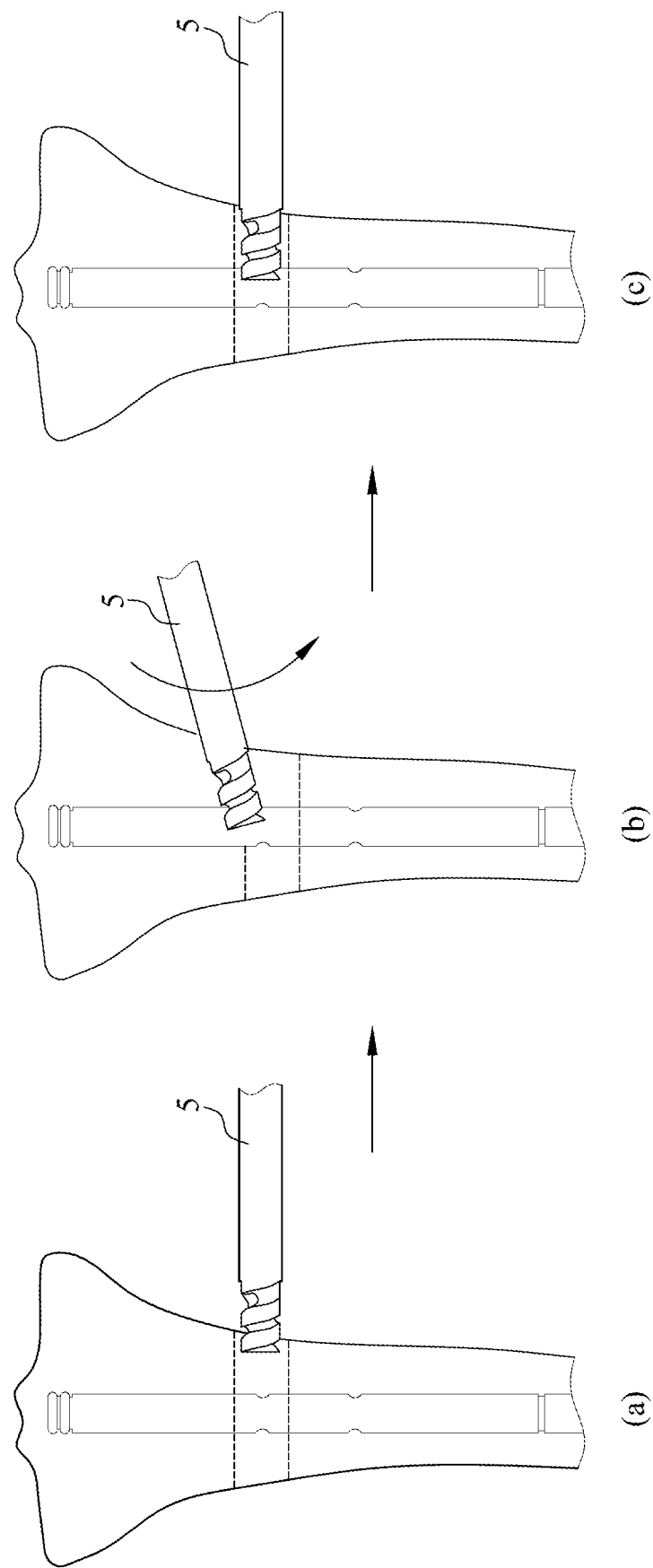
FIG. 9 is a schematic view illustrating the handheld robot of the present invention being used for drilling in the intramedullary interlocking screw fixation surgery, wherein the tool deviates from the path of the predetermined operation plan with an angle.
Figure 10:
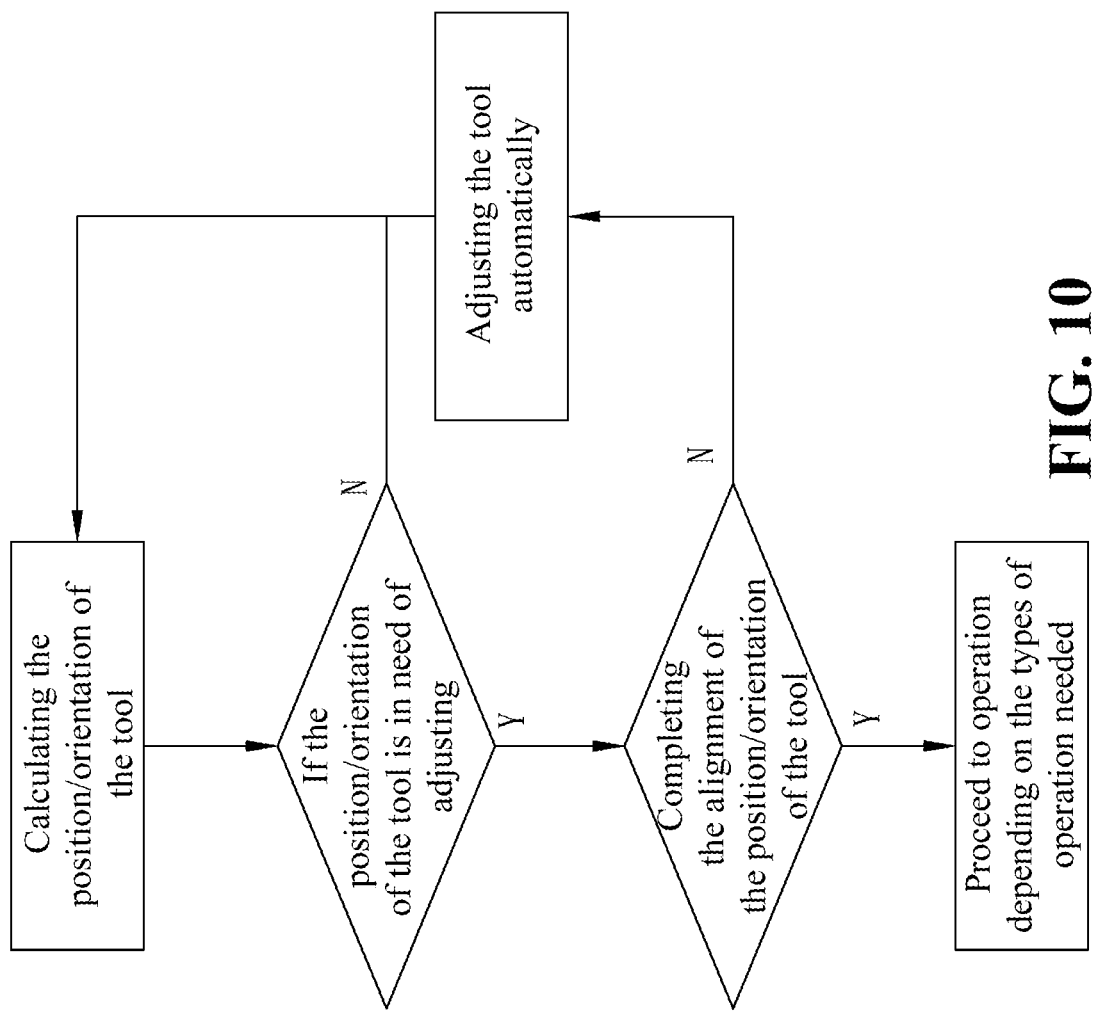
FIG. 10 is a flow chart showing a control method of the present invention, wherein the position and the orientation of the tool is adjusted based on the position/orientation information acquired by a positioning unit.

FIG. 6 and FIG. 7 are schematic views illustrating the handheld robot 100 of the present invention being used for drilling in a bone plate fixation surgery; and FIG. 8 and FIG. 9 are schematic views illustrating the handheld robot 100 of the present invention being used for drilling in an intramedullary interlocking screw fixation surgery. In FIG. 6~FIG. 9, the user uses the handheld robot 100 of the present invention to drill with automatic positioning function. In FIG. 6(a), FIG. 7(a), FIG. 8(a) and FIG. 9(a), before the tool 5 is in contact with the bone of the patient, the position/orientation of the tool 5 is adjusted based on the position/orientation information acquired by the positioning unit 7. FIG. 10 is a flow chart showing a control method of the present invention, wherein the position/orientation of the tool 5 is adjusted with the assistance of the positioning unit 7 before the tool 5 is in contact with the bone. As shown in FIG. 10, the handheld robot 100 calculates the position/orientation of the tool 5 based on a predetermined operation plan, and also based on the relative position/orientation information of the tool 5 with regard to the bone acquired by the positioning unit 7. If the position/orientation of the tool 5 needs to be adjusted, the handheld robot 100 adjusts the position/orientation of the tool 5 through the kinematic mechanism 3, so tool 5 can be aligned with the position/orientation according to the predetermined operation path, thereby achieving dynamic motion compensation of the tool.

Once the tool 5 is in contact with the bone and the drilling process is started, a force is exerted on the tool 5 by the bone. At this moment, if the bone or the hand of the user moves and causes the tool 5 to deviate from the target position/orientation, the non-threaded segment 52, to be more exact, the diameter difference d' between the non-threaded segment 52 and the threaded segment 51 will collide with bone plates, bone screws or bones, thereby generating a deviation force. As shown in FIG. 6(b) and FIG. 8(b), when the tool 5 or the bone offsets from the predetermined path in a direction, a reaction force is generated between the bone and the tool 5 in a corresponding direction, that is, a force which is orthogonal to the axial direction of the tool 5 is generated therebetween. As shown in FIG. 7(b) and FIG. 9(b), when the tool 5 deviates from the predetermined path 5 with an angle, a torque is generated between the bone and the tool 5. In the above situations, the force sensor detects and measures the force/torque which causes the tool 5 to offset/deviate. The handheld robot 100 then adjust the position/orientation of tool 5 through the kinematic mechanism 3 based on the information acquired by the force sensor 6, so as to keep the tool 5 within the path of the predetermined operation plan, as shown in FIG. 6(c), FIG. 7(c), FIG. 8(c) and FIG. 9(c).

Figure 11:
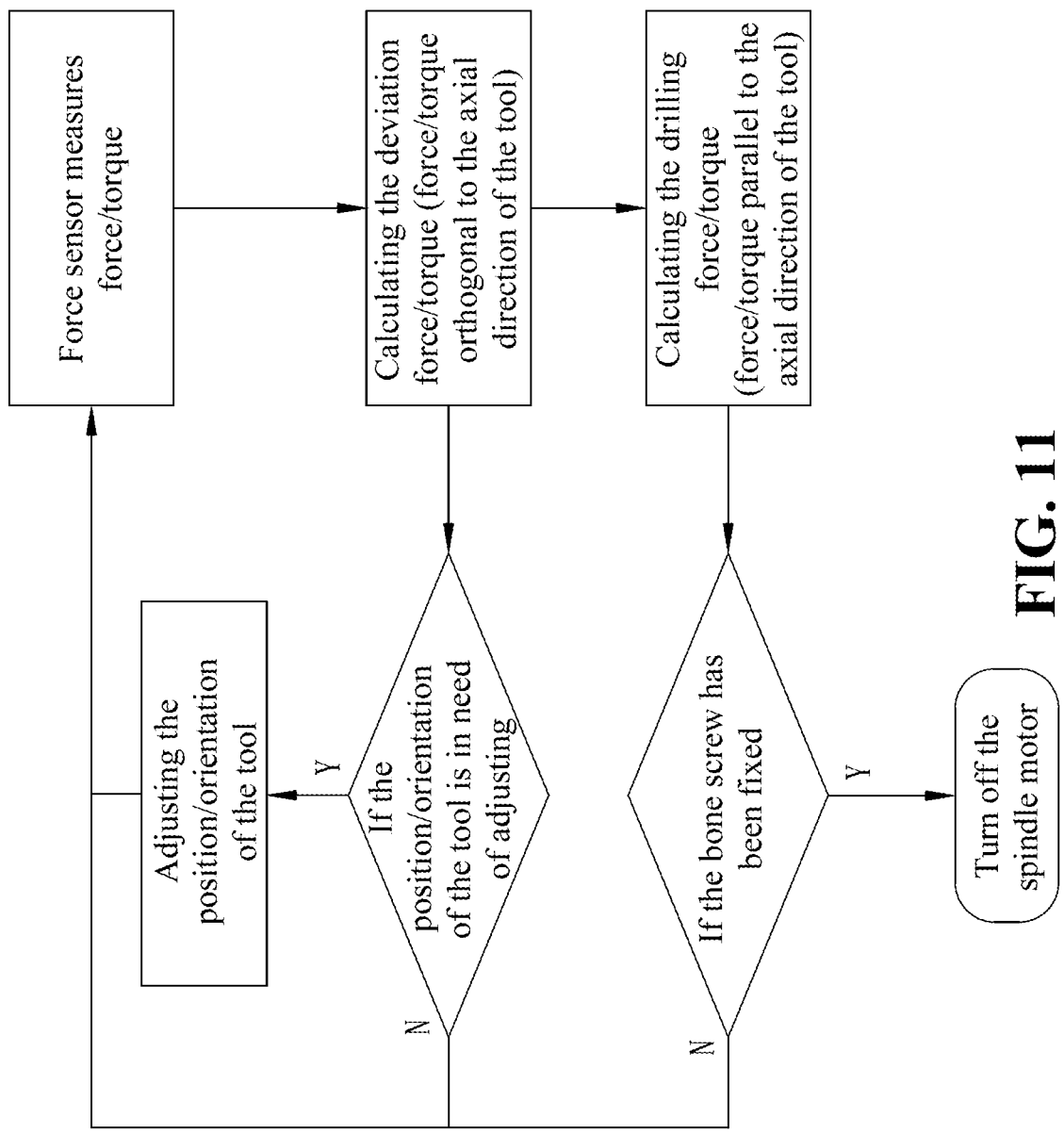
FIG. 11 is a flow chart showing the control method of the present invention, wherein the position/orientation of the tool is adjusted based on the force/torque information acquired by a force sensor, and the handheld robot of the present invention is being used for drilling or tightening bone screws in an operation.

FIG. 11 is a flow chart showing the control method of the present invention, wherein the position/orientation of the tool is adjusted based on the force/torque information acquired by the force sensor 6, and the handheld robot 100 of the present invention is being used for drilling or tightening bone screws in an operation. As shown in FIG. 11, the handheld robot 100 measures the force/torque between the tool 5 and the bone with the force sensor 6 to help with the position/orientation compensation of the tool 5. By calculating the deviation force/torque, the position/orientation of the tool 5 is adjusted to minimize the force/torque orthogonal to the axial direction of the tool and between the tool 5 and the bone, so as to prevent the tool 5 from deviating or offsetting from the path of the predetermined operation plan. The force sensor then measures and calculates the force/torque exerted by the tool 5 during the drilling process, that is, the force which is parallel to the axial direction of the tool 5. The force parallel to the axial direction of the tool 5 is used as a basis for determining if the tool 5 has drilled through the bone, or, as the basis for determining if the bone screw has been completely tightened. If the tool 5 has drilled through the bone or if the bone screw has been completely tightened, the handheld robot 100 then turn off the spindle motor 41, so the tool does not damage other tissues.

The force/torque information acquired by the force sensor 6 as described above can be further combined with the relative information/orientation information of the bone to the tool 5 provided by the positioning unit 7 (e.g. using the multirate Kalman filter for data fusion). As a result, the handheld robot 100 of the present invention is able to achieve dynamic motion compensation quickly and accurately, thereby keeping tool 5 within the path of the predetermined operation plan.

Figure 12:
FIG. 12 is a schematic view illustrating the handheld robot of the present invention being used in an osteotomy.
Figure 13:
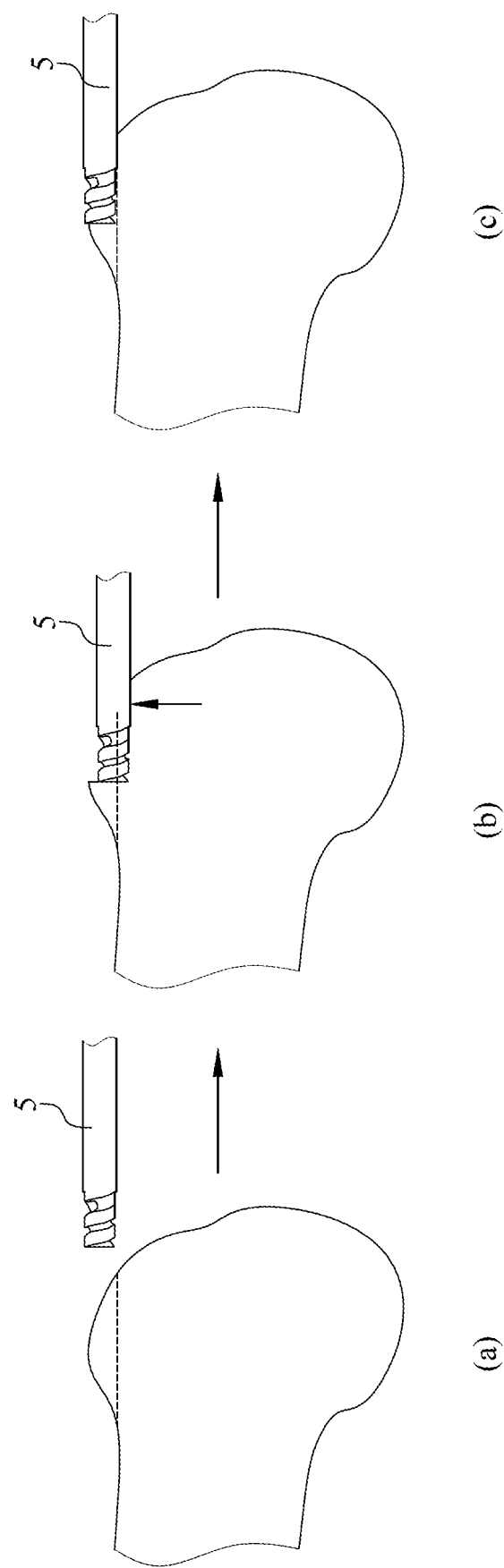
FIG. 13 is a schematic view illustrating the handheld robot of the present invention being used in an osteotomy such as during a total joint replacement surgery, wherein the tool cuts beyond the range of a predetermined operation plan.
Figure 14:
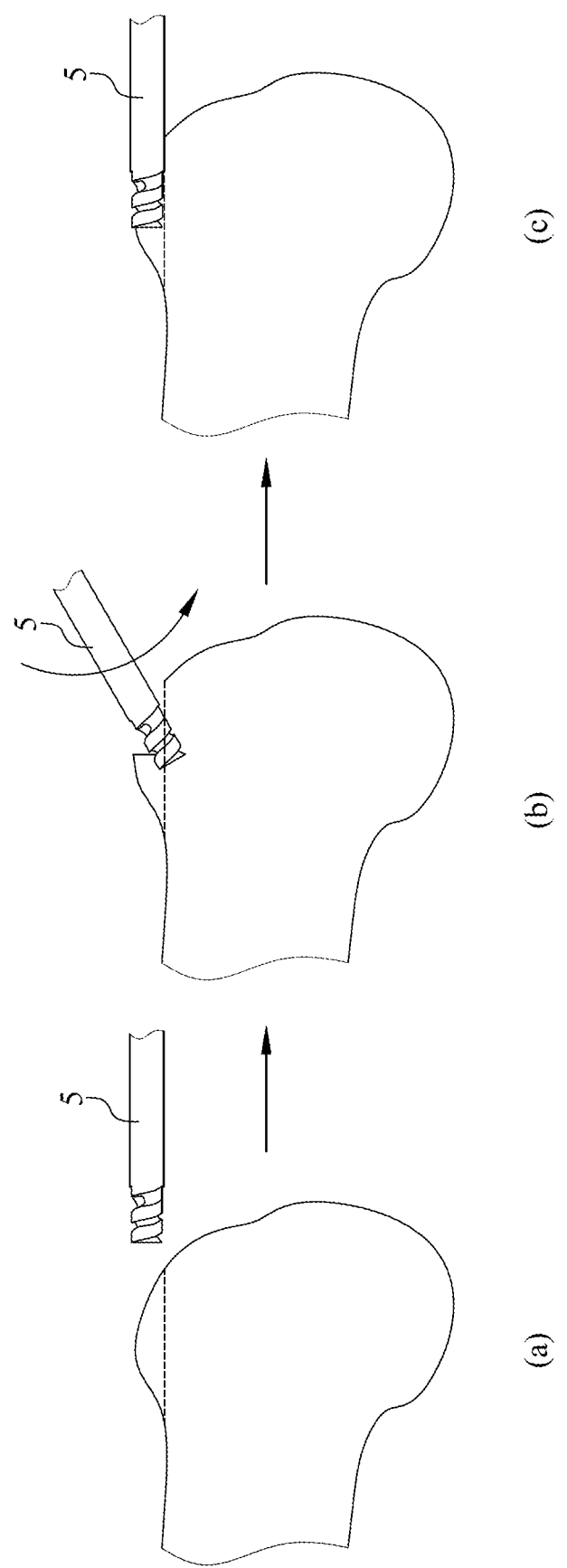
FIG. 14 is a schematic view illustrating the handheld robot of the present invention being used in the osteotomy such as during a total joint replacement surgery, wherein the tool cuts beyond the range of the predetermined operation plan.

FIG. 12~FIG. 14 are schematic views showing the handheld robot 100 of the present invention being used in an osteotomy. In FIG. 13(a) and FIG. 14(a), similar to the situation in which the handheld robot 100 is used for drilling, the position/orientation of tool 5 is adjusted based on the positioning/orientation information provided by the positioning unit 7 before the tool 5 contacts the bone; in other words, the control method in FIG. 10 is used before tool 5 contacts the bone of the patient. Once the cutting begins when the tool 5 contacts the bone, a force is generation between the tool 5 and the bone. At this moment, if the bone or the hand of the user moves and causes the tool 5 to deviate from the target position/orientation, the non-threaded segment 52, to be more exact, the diameter difference d' between the non-threaded segment 52 and the threaded segment 51 will collide with the bone and generate a deviation force. As shown in FIG. 13(b), when the tool 5 or the bone offsets from the range of the predetermined operation plan in a direction, a reaction force is generated in the corresponding direction between the bone and the tool; that is, the reaction force, which is parallel to the normal vector of the cutting surface, is generated between the bone and the tool. As shown in FIG. 14(b), when the tool 5 deviates from the range of the predetermined operation plan with an angle, torques are generated between the bone and the tool 5; to be more exact, two torques, which are orthogonal to the normal vector of the cutting surface, are generated between the bone and the tool 5. After the force sensor 6 measures the deviation force/torque, the position/orientation of tool 5 is adjusted through the kinematic mechanism, so as to keep tool 5 within the range of the predetermined operation plan, as shown in FIG. 13(c) and FIG. 14(c).

Figure 15:
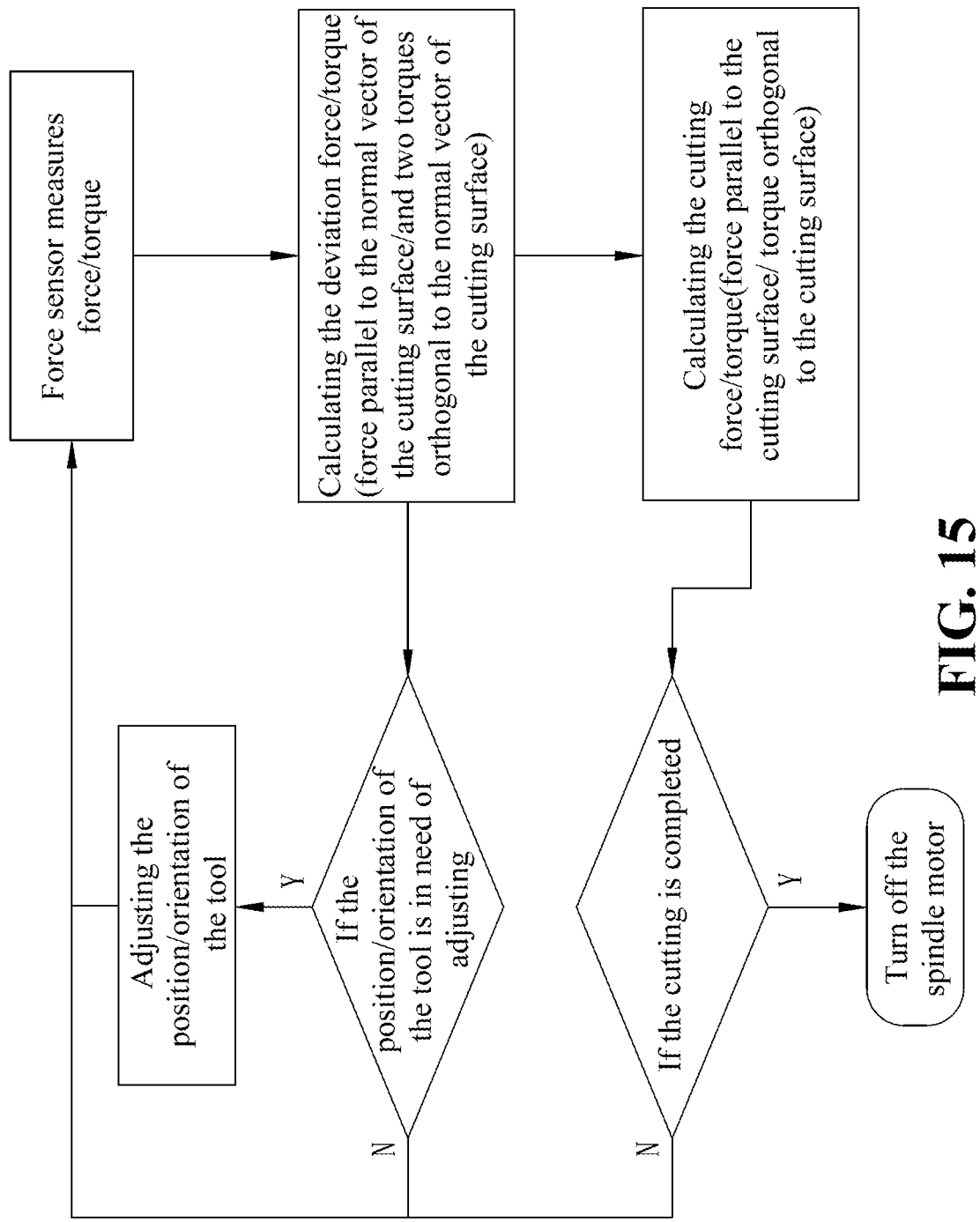
FIG. 15 is a flow chart showing the control method of the present invention, wherein the position/orientation of the tool is adjusted based on the force/torque information measured by the force sensor, and the handheld robot of the present invention is being used in an osteotomy.

FIG. 15 is a flow chart showing the control method of the present invention, wherein the position and the orientation of the tool 5 is adjusted based on the force/torque information measured by the force sensor 6, and the handheld robot 100 of the present invention is being used in an osteotomy. As shown in FIG. 15, the handheld robot 100 of the present invention measures the force/torque between the tool 5 and the bone for the position/orientation compensation of tool 5. By calculating the deviation force/torque, the position/orientation of the tool 5 is adjusted to minimize the force parallel to the normal vector of the cutting surface, and also minimize the two toques orthogonal to the normal vectors of the cutting surface, so as to prevent the tool 5 from deviating or offsetting from the range of the predetermined operation plan. In addition, the cutting force measured by the force sensor, in other words, the force parallel to the cutting surface and the torques orthogonal to the cutting surface are used as the basis for determining if tool 5 has complete the cutting. Referring to FIG. 12, once the tool 5 has passed the dotted line in FIG. 12 and completed cutting, the handheld robot 100 then turns off the spindle motor 41 to prevent tool 5 from damaging other tissues of the patient.

Similarly, the force/torque information acquired by the force sensor 6 as described above can be further combined with the relative information/orientation information of the bone with regard to the tool 5 provided by the positioning unit 7 (e.g. using the multirate Kalman filter for data fusion). As a result, the handheld robot 100 of the present invention is able to achieve dynamic motion compensation quickly and accurately, thereby keeping tool 5 within the range of the predetermined operation plan.

Figure 16:
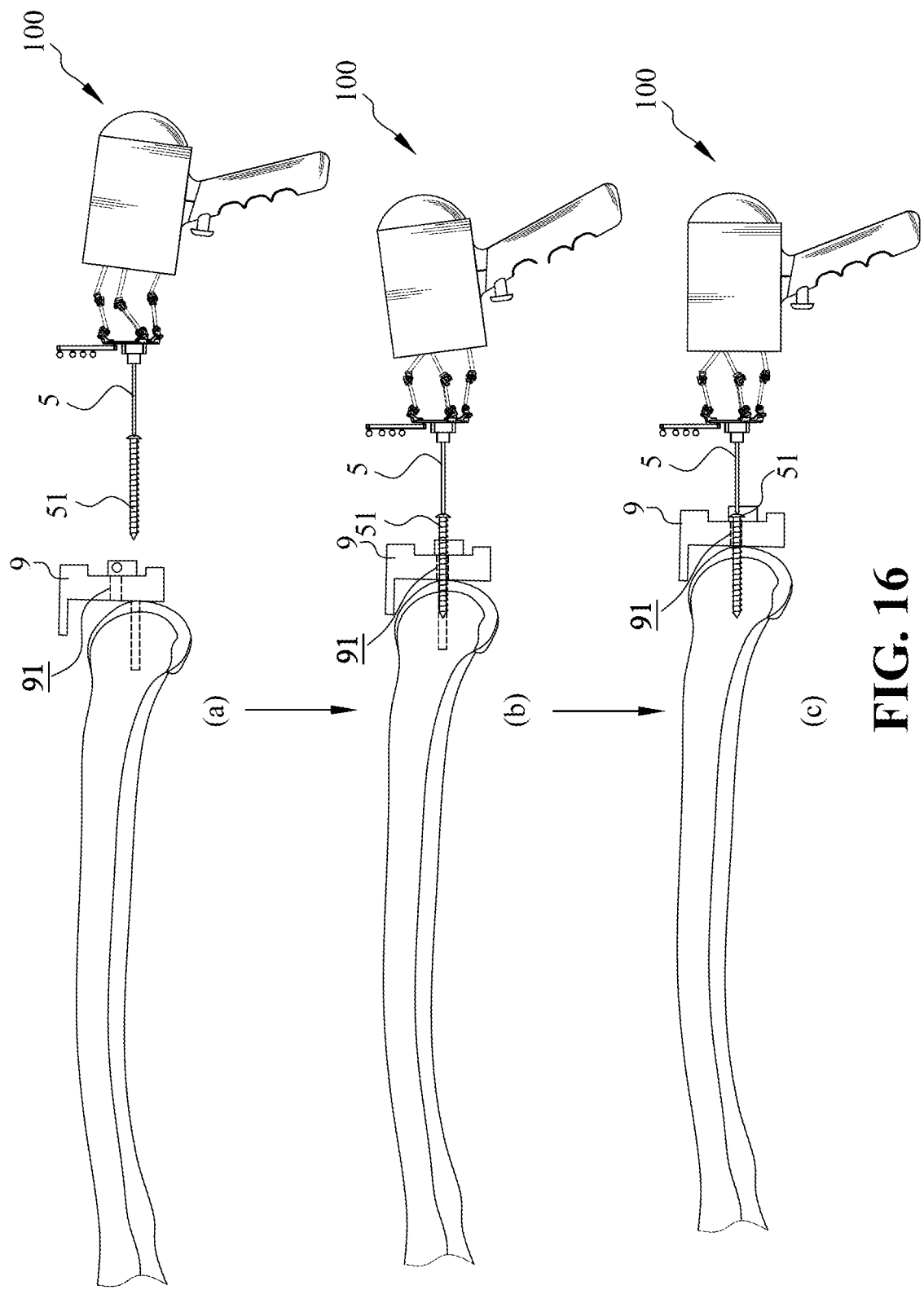
FIG. 16 is a schematic view illustrating the handheld robot of the present invention being used to fix a cutting block.

FIG. 16 is a schematic view illustrating the handheld robot 100 of the present invention being used to fix a cutting block 9. First, as shown in FIG. 16(a), the user manually places the cutting block 9 at certain position/orientation with regard to the bone of the patient as guided by a medical image or computer navigation program. During the process, if the position/orientation of the cutting block 9 is slightly off from the desired position/orientation, the handheld robot 100 of the present invention can adjust the position/orientation of the screw driver and the bone screw 55 at the front thereof through the kinematic mechanism 3 based on the relative position/orientation information of the tool 5 with regard to the bone, and at the same time guides the fixing hole 91 of the cutting block 9 to the desired position/orientation as instructed by the navigation program, as shown in FIG. 16(b). Once the bone screw 55 enters the bone, there are two approaches to fix the cutting block 9 with the handheld robot 100. The first approach to fix the cutting block 9 is to use the control method for drilling as described above. The position/orientation of the screw driver is adjusted through kinematic mechanism 3 based on the force/torque information provided by the force sensor 6 to minimize the force/torque orthogonal to the axial direction of the screw driver. The force/toque measured in the direction parallel to the axial direction of the screw drive can be used as the basis for determining if the bone screw 51 has been tightened. Meanwhile, the handheld robot 100 performs fast and accurate dynamic motion compensation with the relative position/orientation information of the tool with regard to the bone provided by the positioning unit 7. Once the bone screw 51 is tightened as shown in FIG. 16(c), the handheld robot 100 turns off the spindle motor 41. When taking the second approach to fix the cutting block 9, the handheld robot 100 is switched to a manual mode. In the manual mode, the position/orientation of the screw driver is no longer adjusted through the kinematic mechanism 3; instead, the user adjusts the position/orientation of the screw driver manually. In the second approach, the rest of the motion can be easily finished manually because the bone screw 51 has already passed through the fixing hole 91 of the cutting block 9 and is guided to the correct position/orientation with regard to the bone.

Figure 17:
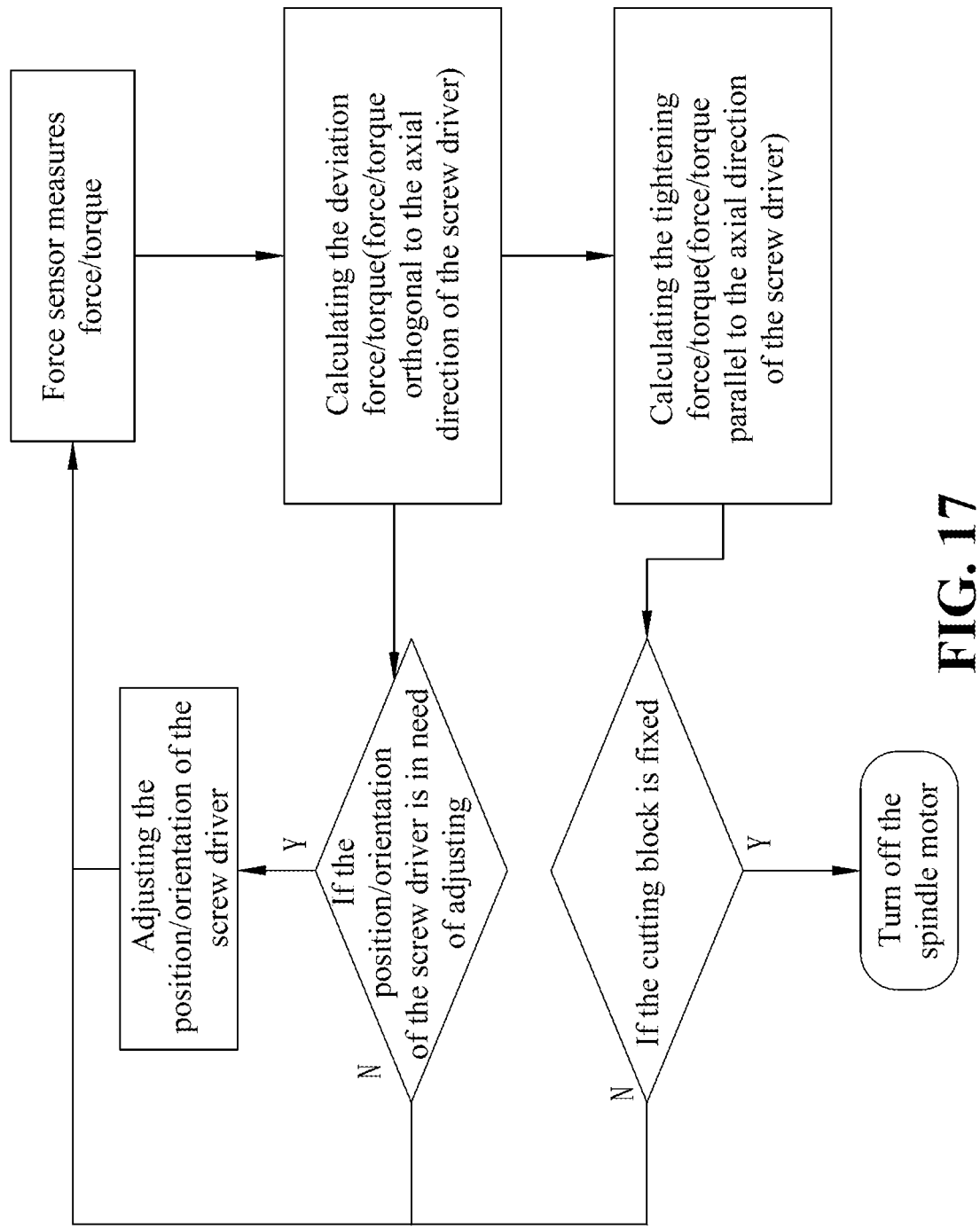
FIG. 17 is a flow chart showing the control method of the present invention, wherein the position/orientation of the tool is adjusted based on the force/torque information measured by the force sensor, and the handheld robot of the present invention is being used to fix a cutting block.

FIG. 17 is a flow chart showing the control method of the present invention, wherein the position/orientation of the tool is adjusted based on the force/torque information measured by the force sensor 6, and the handheld robot 100 of the present invention is being used to fix the cutting block 9.

As shown in FIG. 17, the handheld robot 100 of the present invention measures the force/torque between the tool 5 and the bone to assist with the position/orientation compensation of tool 5. By calculating the deviation force/torque, the position/orientation of the tool 5 is adjusted to minimize the force orthogonal to the axial direction of the screw driver, so as to prevent the tool 5 from deviating or offsetting from the path of the predetermined operation plan. The tightening force/torque measured by the force sensor 6, that is, the force, which is parallel to the axial direction of the screw driver, is used as the basis for determining if the cutting block 9 has been completely fixed. Once the cutting block 9 is fixed, the handheld robot 100 then stops the spindle motor 41 to prevent the tool 5 from damaging other tissues.

The present invention utilizes the spatial information of the tool 5 and the bone of the patient provided by the positioning unit 7 and the force/torque information measured by the force sensor 6 for data fusion, thereby improving the reaction speed of the motion compensation of the tool 5. Generally speaking, due to the bandwidth of the optical positioning system, certain latency is expected in the reaction to the optical positioning system. Therefore, if surgical equipment only uses the spatial information provided by the optical positioning system as the basis of the motion compensation of the front tool thereof, the error accumulated between the spatial information acquired and the actual spatial information could be too large. In comparison, the reaction speed of surgical equipment to the force/torque information is faster; therefore, by utilizing the spatial information in coordination with the force/torque information, the reaction speed of the surgical equipment can be enhanced. By using the control method of the present invention to adjust the position/orientation of the tool at the front of the surgical equipment, the error between the acquired spatial information and the actual spatial information is greatly reduced, thereby improving the precision of the operation. In the meantime, the latency in using the optical positioning system can be reduced, and the blockage situation, which causes the position of the tool to be unreadable, in using the optical positioning system can also be prevented, thereby improving the safety of the operation.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A control method for controlling a robot, comprising:
receiving an operation plan with a predetermined range, a predetermined path, or a combination thereof;
measuring a deviation force, a deviation torque, or a combination thereof that is generated between a threaded segment and a non-threaded segment of a tool and deviates the tool from the predetermined range, the predetermined path, or the combination thereof, of the received operation plan; and
adjusting at least one of the position and the orientation of the tool based on the measured deviation force, the measured deviation torque, or the combination thereof, so as to keep the tool within the predetermined range, the predetermined path, or the combination thereof, of the received operation plan.

2. The method according to claim 1, further comprising:
acquiring position information, orientation information, or a combination thereof, of the tool; and
adjusting at least one of the position and the orientation of the tool based on the acquired position information, the acquired orientation information, or the combination thereof, so as to keep the tool within the predetermined range, the predetermined path, or the combination thereof, of the received operation plan.

3. The method according to claim 2, further comprising combining the acquired position information, the acquired orientation information, or the combination thereof with the measured deviation force, the measured deviation torque, or the combination thereof, wherein the adjusting steps are performed based on result information of the combining.

4. The method according to claim 1, wherein when the robot is used for drilling, the deviation force, the deviation torque, or the combination thereof includes a force, a torque, or a combination thereof orthogonal to an axial direction of the tool.

5. The method according to claim 1, wherein when the robot is used for drilling, the method further comprises calculating a drilling force, a drilling torque, or a combination thereof which is parallel to an axial direction of the tool to determine if the drilling is completed.

6. The method according to claim 1, wherein when the robot is used for cutting, the deviation force, the deviation torque, or the combination thereof includes a force parallel to a normal vector of a cutting surface, and includes two torques that are orthogonal to the normal vector of the cutting surface.

7. The method according to claim 1, wherein when the robot is used for cutting, the method further comprises calculating a combination of a cutting force and a cutting torque which includes a force parallel to a cutting surface and a torque orthogonal to the cutting surface to determine if the cutting is completed.

8. A control method for controlling a robot, comprising:
receiving an operation plan with a predetermined range, a predetermined path, or a combination thereof;
measuring a force, a torque, or a combination thereof that is generated between a threaded segment and a non-threaded segment of a tool;
calculating at least one of the measured force and the measured torque orthogonal to an axial direction of the tool that deviates the tool from the predetermined range, the predetermined path, or the combination thereof, of the received operation plan; and
adjusting at least one of a position and an orientation of the tool to minimize a calculated deviation force, a calculated deviation torque, or a combination thereof, so as to keep the tool within the predetermined range, the predetermined path, or the combination thereof, of the received operation plan.

9. The method according to claim 8, further comprising calculating at least one of a drilling force parallel to the axial direction of the tool and a drilling torque parallel to the axial direction of the tool, to determine if a drilling is completed.

10. The method according to claim 8, further comprising:
acquiring position information, orientation information, or a combination thereof, of the tool; and
adjusting at least one of the position and the orientation of the tool based on the acquired position information, the acquired orientation information, or the combination thereof, so as to keep the tool within the predetermined range, the predetermined path, or the combination thereof, of the received operation plan.

11. The method according to claim 10, further comprising combining the acquired position information, the acquired orientation information, or the combination thereof with the measured force, the measured torque, or the combination thereof, wherein the adjusting steps are performed based on result information of the combining.

12. A control method for controlling a robot, comprising:
receiving an operation plan with a predetermined range, a predetermined path, or a combination thereof;
measuring a force, a torque, or a combination thereof that is generated between a threaded segment and a non-threaded segment of a tool;
calculating the measured force parallel to a normal vector of a cutting surface and two torques orthogonal to the normal vector of the cutting surface that deviate the tool from the predetermined range, the predetermined path, or the combination thereof, of the received operation plan; and
adjusting at least one of a position and an orientation of a tool to minimize a calculated deviation force, calculated deviation torques, or a combination thereof, so as to keep the tool within the predetermined range, the predetermined path, or the combination thereof, of the received operation plan.

13. The method according to claim 12, further comprising calculating at least one of a cutting force parallel to the cutting surface and a cutting torque orthogonal to the cutting surface, to determine if a cutting is completed.

14. The method according to claim 12, further comprising:
acquiring position information, orientation information, or a combination thereof, of the tool; and
adjusting at least one of the position and the orientation of the tool based on the acquired position information, the acquired orientation information, or the combination thereof, so as to keep the tool within the predetermined range, the predetermined path, or the combination thereof, of the received operation plan.

15. The method according to claim 14, further comprising combining the acquired position information, the acquired orientation information, or the combination thereof with the measured force, the measured torques, or the combination thereof, wherein the adjusting steps are performed based on result information of the combining.

* * * * *